ated under 35

(12) United States Patent  
Goto et al.

(10) Patent No.: US 10,676,463 B2  
(45) Date of Patent: Jun. 9, 2020

(54) MONOGLYCIDYL ISOCYANURATE COMPOUND AND PRODUCTION METHOD THEREFOR

(71) Applicant: NISSAN CHEMICAL CORPORATION, Tokyo (JP)

(72) Inventors: Yuichi Goto, Toyama (JP); Masahisa Endo, Toyama (JP); Gun Son, Toyama (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 16/091,770

(22) PCT Filed: Mar. 24, 2017

(86) PCT No.: PCT/JP2017/012126  
§ 371 (c)(1),  
(2) Date: Oct. 5, 2018

(87) PCT Pub. No.: WO2017/175610  
PCT Pub. Date: Oct. 12, 2017

(65) Prior Publication Data  
US 2019/0135795 A1    May 9, 2019

(30) Foreign Application Priority Data

Apr. 7, 2016    (JP) .................. 2016-077388

(51) Int. Cl.  
*C07D 405/06* (2006.01)  
*C07D 251/34* (2006.01)

(52) U.S. Cl.  
CPC ......... *C07D 405/06* (2013.01); *C07D 251/34* (2013.01)

(58) Field of Classification Search  
CPC ................ C07D 251/34; C07D 405/04  
USPC ..................................... 544/221  
See application file for complete search history.

(56) References Cited

U.S. PATENT DOCUMENTS

| 3,065,231 A | * | 11/1962 | Frazier, Jr. | ............ | C07D 251/34 544/221 |
| 3,249,607 A | * | 5/1966 | Taub | ............ | C07D 251/34 544/221 |
| 4,260,505 A | * | 4/1981 | Milnes | ............ | C07D 251/34 252/77 |
| 4,529,779 A | * | 7/1985 | Arai | ............ | C08G 63/685 525/410 |
| 8,987,358 B2 | * | 3/2015 | Kawabata | ............ | C07F 7/21 524/101 |

FOREIGN PATENT DOCUMENTS

| JP | S55-080431 A | 6/1980 |
| JP | S60-197674 A | 10/1985 |
| JP | 3902140 B2 | 4/2007 |

(Continued)

OTHER PUBLICATIONS

PubChem Search—Compounds 1-10, Create Date Dec. 5, 2007 to Create Date Feb. 13, 2015. PubChem Search results provided.*  
PubChem Search2—Compounds 1-50, Create Date Mar. 26, 2005 to Create Date Jan. 24, 2017, PubChem Search results provided.*  
Apr. 18, 2017 International Search Report issued in International Patent Application No. PCT/JP2017/012126.  
Apr. 18, 2017 Written Opinion of the International Searching Authority issued in International Patent Application No. PCT/JP2017/012126.

*Primary Examiner* — Venkataraman Balasubramanian  
(74) *Attorney, Agent, or Firm* — Oliff PLC

(57) ABSTRACT

There are provided a novel isocyanurate compound having a glycidyl group as a substituent to be bonded to a nitrogen atom. A monoglycidyl isocyanurate compound of the following Formula (1), (2), or (3).

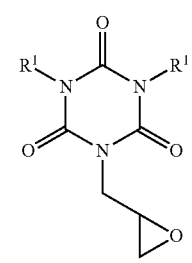

(1)

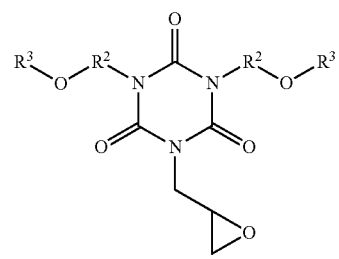

(2)

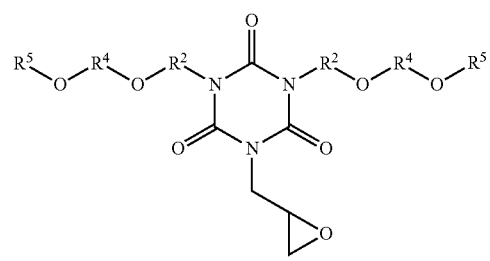

(3)

(wherein two $R^1$s are each a $C_{2-10}$ alkyl group, two $R^2$s are each a $C_{1-5}$ alkylene group, two $R^3$s are each a $C_{1-2}$ alkyl group, two $R^4$s are each a $C_{1-2}$ alkylene group, and two $R^5$s are each a $C_{1-2}$ alkyl group).

6 Claims, No Drawings

(56) References Cited

FOREIGN PATENT DOCUMENTS

| JP | 2007-238472 A | 9/2007 |
|----|---------------|--------|
| JP | 2012-025688 A | 2/2012 |
| JP | 2013-032327 A | 2/2013 |

* cited by examiner

MONOGLYCIDYL ISOCYANURATE COMPOUND AND PRODUCTION METHOD THEREFOR

TECHNICAL FIELD

The present invention relates to a novel isocyanurate compound having a glycidyl group as a substituent to be bonded to a nitrogen atom, and a method for producing the same.

BACKGROUND ART

An isocyanuric acid derivative having at least one glycidyl group has been conventionally known. For example, Patent Document 1 discloses triglycidyl isocyanurate, monoallyl diglycidyl isocyanurate, and diallyl monoglycidyl isocyanurate. Patent Document 1 states that an epoxy resin composition obtained by mixing triglycidyl isocyanurate, monoallyl diglycidyl isocyanurate, and/or diallyl monoglycidyl isocyanurate is suitable for an adhesive, a coating, a mold material, a layering material, and the like. Patent Document 2 discloses a monoglycidylisocyanuric acid compound that can solve a problem of 1,3-diallyl-5-glycidylisocyanuric acid. However, the monoglycidylisocyanuric acid compound synthesized in Patent Document 2 has two aromatic rings in the molecule, and therefore, the solubility thereof in an organic solvent may be low.

Patent Document 3 discloses a method in which an isocyanuric acid derivative having at least one glycidyl group and/or at least one allyl group is used as a starting material to synthesize an alkenyl compound, the alkenyl compound is used as a reaction intermediate to synthesize an epoxy compound. Further, Patent Document 3 discloses a resist underlayer film-forming composition using the synthesized epoxy compound.

PRIOR ART DOCUMENTS

Patent Documents

Patent Document 1: Japanese Patent No. 3902140
Patent Document 2: Japanese Patent Application Publication No. 2007-238472 (JP 2007-238472 A)
Patent Document 3: Japanese Patent Application Publication No. 2013-32327 (JP 2013-32327 A)

SUMMARY OF THE INVENTION

Problem to be Solved by the Invention

For example, an object of the present invention is to provide a novel isocyanurate compound, which is expected to be used as a raw material for a resist underlayer film-forming composition.

Means for Solving the Problems

The inventor of the present invention has found that an isocyanurate compound having a glycidyl group as a substituent to be bonded to a nitrogen atom is obtained by using monoallyl isocyanuric acid (also referred to as monoallyl isocyanurate) as a starting material. That is, an aspect of the present invention is a monoglycidyl isocyanurate compound of the following Formula (1), (2), or (3):

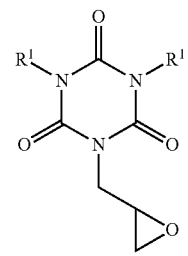

(1)

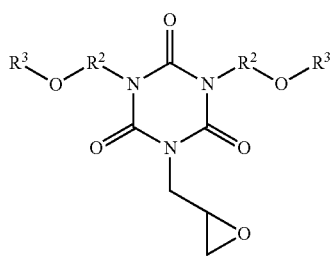

(2)

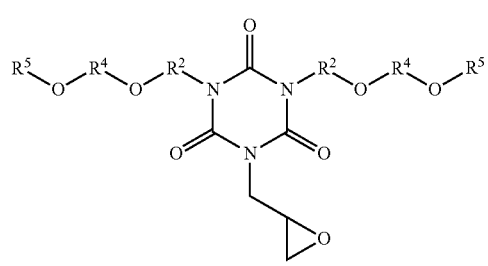

(3)

(wherein two $R^1$s are each a $C_{2-10}$ alkyl group, two $R^2$s are each a $C_{1-5}$ alkylene group, two $R^3$s are each a $C_{1-2}$ alkyl group, two $R^4$s are each a $C_{1-2}$ alkylene group, and two $R^5$s are each a $C_{1-2}$ alkyl group).

For example, the two $R^1$s are each a $C_{2-3}$ alkyl group.

For example, the two $R^2$s are each a $C_{1-2}$ alkylene group.

For example, the two $R^3$s are each methyl group.

For example, the monoglycidyl isocyanurate compound of Formula (2) or (3) is liquid at normal temperature under normal pressure when the total number of carbon atoms and oxygen atoms of a —$R^2OR^3$ group in Formula (2) or a —$R^2OR^4OR^5$ group in Formula (3) is four or more. Herein, at normal temperature under normal pressure in the specification is defined as a temperature of 20° C. to 25° C. and an air pressure of 101 kPa.

Another aspect of the present invention is a method for producing a monoglycidyl isocyanurate compound comprising the steps of obtaining a reaction intermediate of the following Formula (1'), (2'), or (3'):

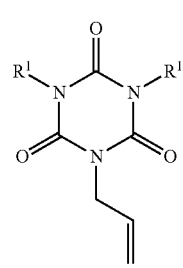

(1')

-continued

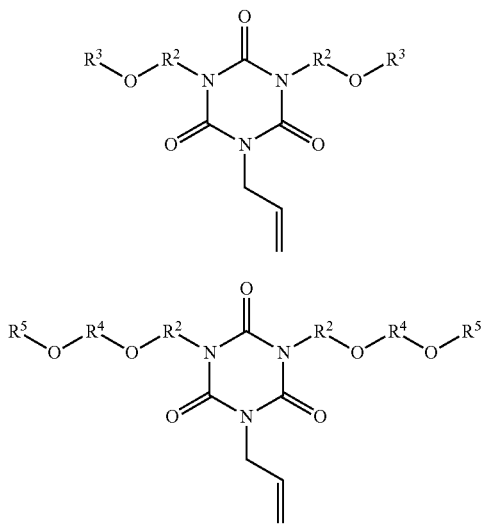

(wherein two R$^1$s are each a C$_{2-10}$ alkyl group, two R$^2$s are each a C$_{1-5}$ alkylene group, two R$^3$s are each a C$_{1-2}$ alkyl group, two R$^4$s are each a C$_{1-2}$ alkylene group, and two R$^5$s are each a C$_{1-2}$ alkyl group) from monoallyl isocyanuric acid, and reacting the reaction intermediate of Formula (1'), (2'), or (3') with an oxidant.

The reaction intermediate of Formula (1'), (2'), or (3') is obtained, for example, by reacting the monoallyl isocyanuric acid with a compound of the following Formula (a), (b), or (c):

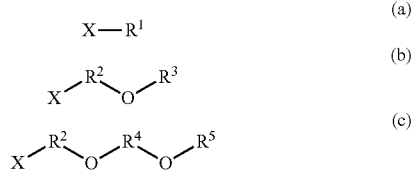

(wherein X is a chloro group, a bromo group, or an iodo group, R$^1$ is a C$_{2-10}$ alkyl group, R$^2$ is a C$_{1-5}$ alkylene group, R$^3$ is a C$_{1-2}$ alkyl group, R$^4$ is a C$_{1-2}$ alkylene group, and R$^5$ is a C$_{1-2}$ alkyl group).

The oxidant is, for example, m-chloroperbenzoic acid or hydrogen peroxide.

Effects of the Invention

The monoglycidyl isocyanurate compound of the present invention is expected to be used as a raw material for a polymer or oligomer component of a resist underlayer film-forming composition and the like. The monoglycidyl isocyanurate compound of the present invention has excellent solubility in an organic solvent (propylene glycol monomethyl ether) used for the resist underlayer film-forming composition and the like. Further, a reaction product of the monoglycidyl isocyanurate compound with a multifunctional carboxylic acid, multifunctional phenol, or multifunctional thiophenol etc. is expected to improve solubility as well as etching rate of a film formed from a resist underlayer film-forming composition containing the reaction product.

MODES FOR CARRYING OUT THE INVENTION

The monoglycidyl isocyanurate compound of the present invention is represented by Formula (1), (2), or (3) described above. In Formula (1), a C$_{2-10}$ alkyl group of R$^1$ may be a linear, branched, or cyclic group. Examples of the alkyl group include ethyl group, n-propyl group, isopropyl group, n-butyl group, isobutyl group, n-pentyl group, n-hexyl group, n-heptyl group, n-octyl group, n-pentyl group, n-nonyl group, n-decyl group, cyclohexylmethyl group, and cyclopentylmethyl group.

Examples of C$_{1-5}$ alkylene group of R$^2$ in Formulae (2) and (3) include methylene group, ethylene group, propylene group, trimethylene group, butylene group, and pentylene group. In Formula (2), R$^3$ is a C$_{1-2}$ alkyl group. Examples of the C$_{1-2}$ alkyl group include methyl group and ethyl group. Examples of C$_{1-2}$ alkylene group of R$^4$ in Formula (3) include methylene group and ethylene group. Examples of the C$_{1-2}$ alkyl group of R$^5$ in Formula (3) include methyl group and ethyl group.

Examples of the monoglycidyl isocyanurate compound of the present invention include compounds of the following Formulae (1-1) to (1-13), (2-1) to (2-5), and (3-1) to (3-4).

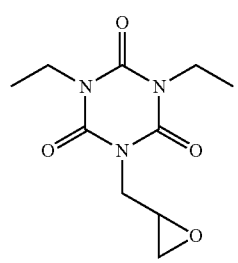

(1-1)

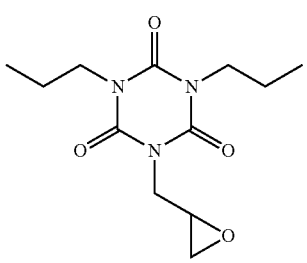

(1-2)

-continued
(1-3)
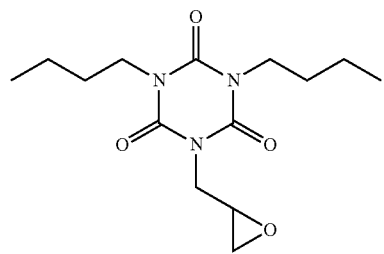
(1-4)
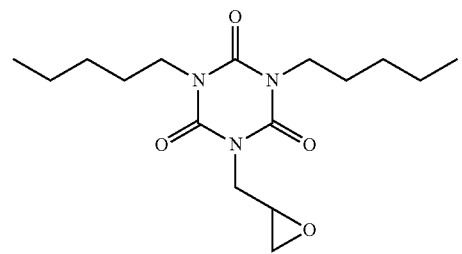
(1-5)
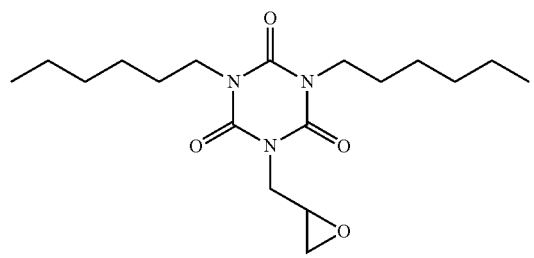
(1-6)
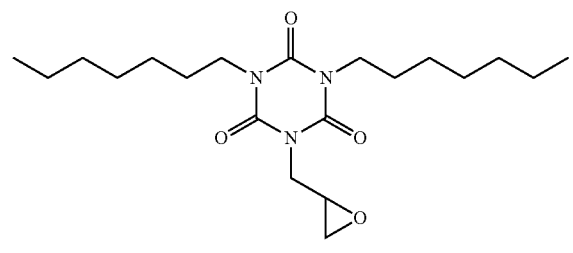
(1-7)
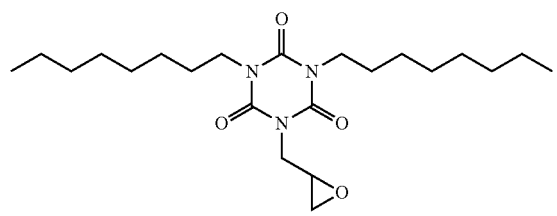
(1-8)
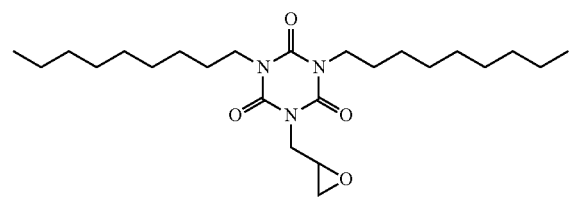
(1-9)
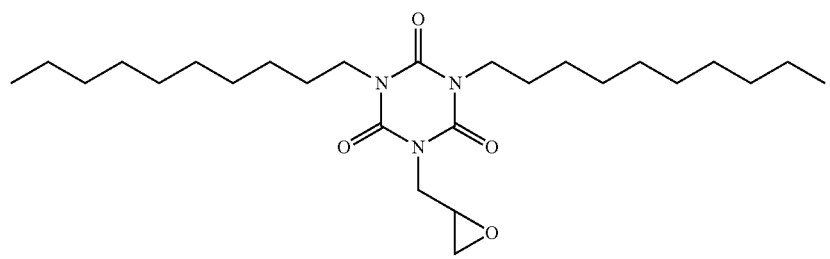
(1-10)
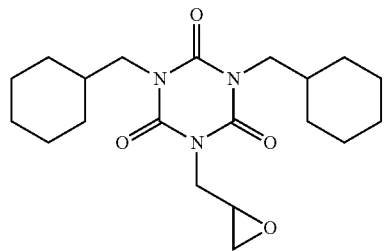
(1-11)
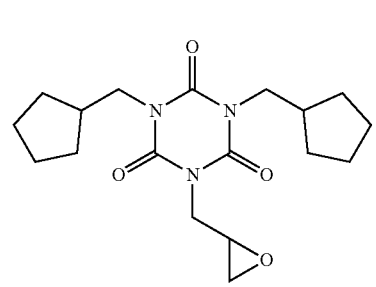
(1-12)
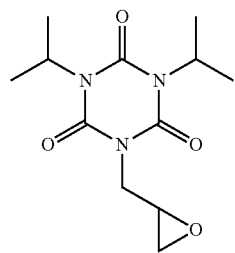
(1-13)
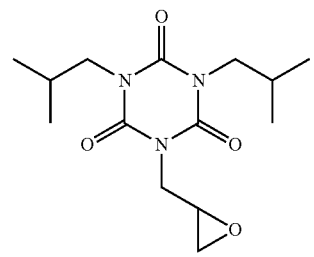

-continued
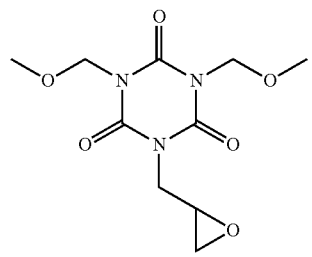
(2-1)
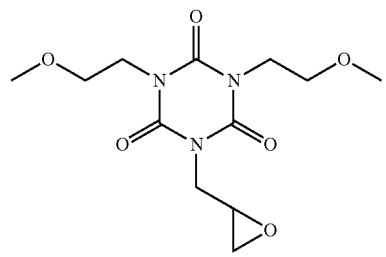
(2-2)
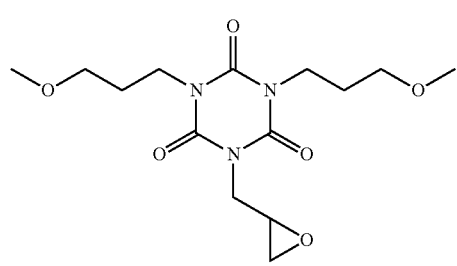
(2-3)
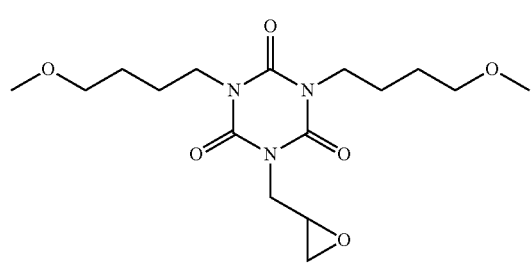
(2-4)
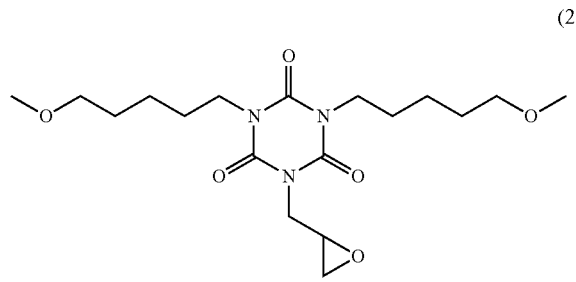
(2-5)
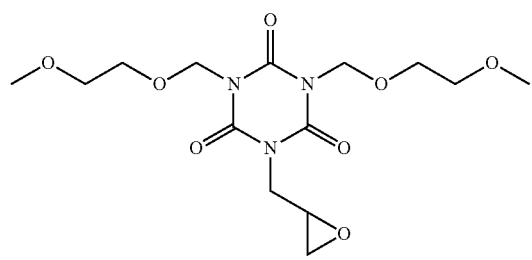
(3-1)
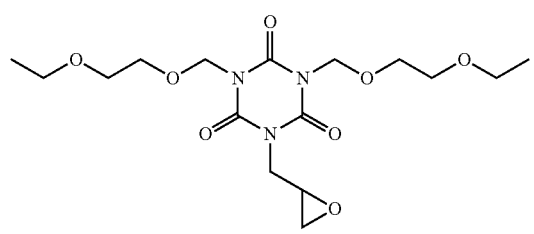
(3-2)
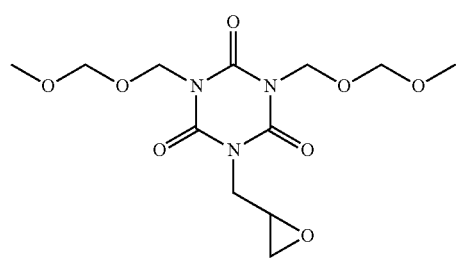
(3-3)
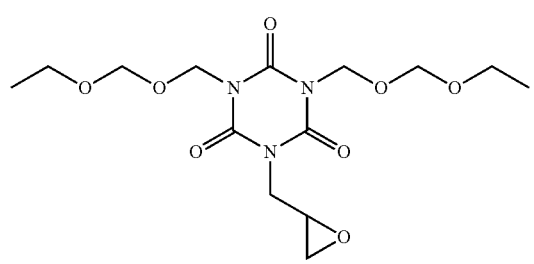
(3-4)

EXAMPLES

Hereinafter, the monoglycidyl isocyanurate compound according to the present invention will be described with reference to specific examples. However, the present invention is not necessarily limited to the specific examples described below.

Synthesis Example 1

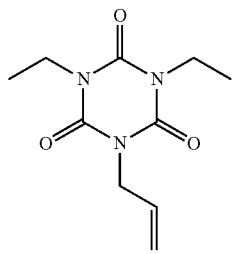

(4)

25.00 g of monoallyl isocyanuric acid (product name: MA-IC, available from Shikoku Chemicals Corporation), 51.07 g of potassium carbonate, and 125.00 g of N-methylpyrrolidone were mixed and stirred at 25° C. To the mixture, 40.27 g of bromoethane (available from Tokyo Chemical Industry Co., Ltd.) was added dropwise. After completion of dropwise addition, the mixture was stirred at 25° C. for 5.5 hours to obtain a reaction solution. To the reaction solution, 250.00 g of toluene was added, and the solution was filtered. A cake was washed with 25.00 g of toluene twice. After washing, 250.00 g of water was added to the obtained solution, resulting in separation. This separation operation was repeated three times. From the organic phase, a solvent was distilled off under reduced pressure, and the residue was then dried at 40° C. under reduced pressure. 30.16 g of diethyl monoallyl isocyanurate of Formula (4) above was obtained as a liquid (yield: 90.6%). This compound was subjected to $^1$H NMR measurement (500 MHz, CDCl$_3$). δ 5.88 (ddt, 1H), 5.31 (dd, 1H), 5.23 (dd, 1H), 4.48 (d, 2H), 3.95 (q, 4H), 1.24 (t, 6H)

In the specification, a NMR apparatus used in $^1$H NMR measurement was JNM-ECA500 manufactured by JEOL Ltd.

Synthesis Example 2

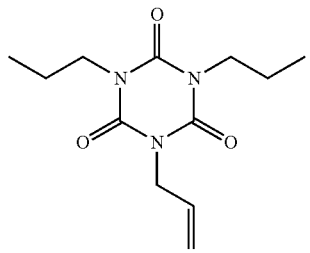

(5)

25.00 g of monoallyl isocyanuric acid (product name: MA-IC, available from Shikoku Chemicals Corporation), 51.07 g of potassium carbonate, and 125.00 g of N-methylpyrrolidone were mixed and stirred at 25° C. To the mixture, 45.45 g of bromopropane (available from Tokyo Chemical Industry Co., Ltd.) was added dropwise. After completion of dropwise addition, the temperature was increased to 60° C., and the mixture was stirred for 4 hours to obtain a reaction solution. The reaction solution was cooled to room temperature. To the reaction solution, 250.00 g of toluene was added, and the solution was filtered. A cake was washed with 25.00 g of toluene twice. After washing, 250.00 g of water was added to the obtained solution, resulting in separation. This separation operation was repeated three times. From the organic phase, a solvent was distilled off under reduced pressure, and the residue was then dried at 40° C. under reduced pressure. 36.35 g of dipropyl monoallyl isocyanurate of Formula (5) above was obtained as a liquid (yield: 97.1%). This compound was subjected to $^1$H NMR measurement (500 MHz, CDCl$_3$). δ 5.88 (1H, ddt), 5.29 (1H, dd), 5.23 (1H, dd), 4.48 (2H, d), 3.85 (4H, t), 1.67 (4H, qt), 0.94 (6H, t)

Synthesis Example 3

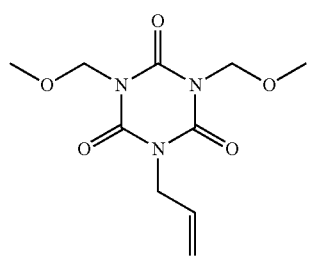

(6)

30.00 g of monoallyl isocyanuric acid (product name: MA-IC, available from Shikoku Chemicals Corporation), 61.29 g of potassium carbonate, and 150.00 g of N-methylpyrrolidone were mixed. To the mixture, 35.70 g of chloromethyl methyl ether (available from Tokyo Chemical Industry Co., Ltd.) was added dropwise with stirring at 25° C. After completion of dropwise addition, a reaction solution was obtained. To the reaction solution, 300.00 g of ethyl acetate was added, and the solution was filtered. A cake was washed with 30.00 g of ethyl acetate twice. After washing, 300.00 g of water was added to the obtained solution, resulting in separation. This separation operation was repeated three times. From the organic phase, a solvent was distilled off under reduced pressure, and the residue was then dried at 40° C. under reduced pressure. 30.63 g of dimethoxymethyl monoallyl isocyanurate of Formula (6) above was obtained as a liquid (yield: 67.1%). This compound was subjected to $^1$H NMR measurement (500 MHz, CDCl$_3$). δ 5.88 (ddt, 1H), 5.34-5.20 (m, 6H), 4.51 (d, 2H), 3.45 (s, 6H)

Synthesis Example 4

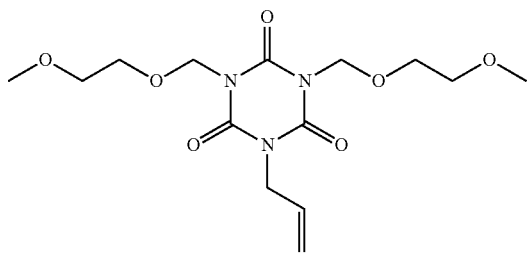

(7)

20.00 g of monoallyl isocyanuric acid (product name: MA-IC, available from Shikoku Chemicals Corporation), 40.86 g of potassium carbonate, and 100.00 g of N-methylpyrrolidone were mixed. To the mixture, 38.76 g of 2-methoxyethoxymethyl chloride (available from Tokyo Chemical Industry Co., Ltd.) was added dropwise with stirring at 25° C. After completion of dropwise addition, a reaction solution was obtained. To the reaction solution, 300.00 g of toluene was added, and the solution was filtered. A cake was washed with 30.00 g of toluene twice. After washing, 300.00 g of water was added to the obtained solution, resulting in separation. This separation operation was repeated three times. From the organic phase, a solvent was distilled off under reduced pressure, and the residue was then dried at 40° C. under reduced pressure. 20.36 g of dimethoxyethoxymethyl monoallyl isocyanurate of Formula (7) above was obtained as a liquid (yield: 49.9%). This compound was subjected to $^1$H NMR measurement (500 MHz, CDCl$_3$). δ 5.87 (ddt, 1H), 5.43 (s, 4H), 5.34 (dd, 1H), 5.24 (dd, 1H), 4.50 (d, 2H), 3.81 (t, 4H), 3.51 (t, 4H), 3.34 (s, 6H)

Synthesis Example 5

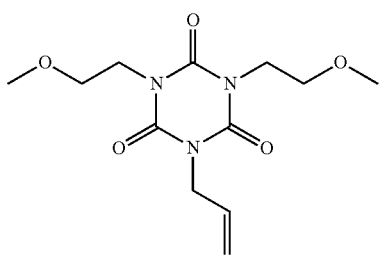

(8)

22.00 g of monoallyl isocyanuric acid (product name: MA-IC, available from Shikoku Chemicals Corporation), 47.58 g of potassium carbonate, and 110.00 g of N-methylpyrrolidone were mixed and stirred at 25° C. To the mixture, 47.57 g of 2-bromoethyl methyl ether (available from Tokyo Chemical Industry Co., Ltd.) was added dropwise. After completion of dropwise addition, a reaction solution was obtained. To the reaction solution, 220.00 g of toluene was added, and the solution was filtered. A cake was washed with 22.00 g of toluene twice. After washing, 220.00 g of water was added to the obtained solution, resulting in separation. This separation operation was repeated three times. From the organic phase, a solvent was distilled off under reduced pressure, and the residue was then dried at 40° C. under reduced pressure. 30.93 g of dimethoxyethyl monoallyl isocyanurate of Formula (8) above was obtained as a liquid (yield: 83.3%). This compound was subjected to $^1$H NMR measurement (500 MHz, CDCl$_3$). δ 5.87 (1H, ddt), 5.29 (1H, dd), 5.23 (1H, dd) 4.49 (2H, d), 4.12 (4H, t) 3.62 (4H, t) 3.35 (6H, s)

Synthesis Example 6

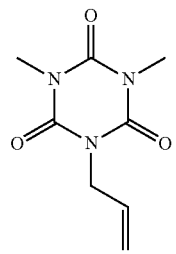

(9)

40.00 g of monoallyl isocyanuric acid (product name: MA-IC, available from Shikoku Chemicals Corporation), 81.73 g of potassium carbonate, and 200.00 g of N-methylpyrrolidone were mixed and stirred at 25° C. To the mixture, 83.92 g of iodomethane (available from Tokyo Chemical Industry Co., Ltd.) was added dropwise. After completion of dropwise addition, the temperature was increased to 105° C., and the mixture was stirred for 2 hours to obtain a reaction solution. To the reaction solution, 400.00 g of toluene was added, and the solution was filtered. A cake was washed with 40.00 g of toluene twice. After washing, 400.00 g of water was added to the obtained solution, resulting in separation. This separation operation was repeated three times. From the organic phase, a solvent was distilled off under reduced pressure, and the residue was then dried at 40° C. under reduced pressure. 39.70 g of dimethyl monoallyl isocyanurate of Formula (9) above was obtained as a white solid (yield: 85.1%).

Example 1

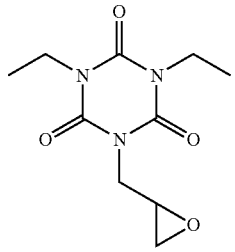

(1-1)

30.00 g of diethyl monoallyl isocyanurate obtained in Synthesis Example 1 and 225.00 g of chloroform were mixed and stirred at 25° C. To the mixture, 42.43 g of m-chloroperbenzoic acid (available from Tokyo Chemical Industry Co., Ltd.) was added. The mixture was stirred at 25° C. for 85.5 hours to obtain a reaction solution. To the reaction solution, 300.00 g of chloroform was added. With stirring, 600.00 g of 5 wt % NaHCO$_3$ was added dropwise, and separation was carried out. To the obtained organic phase, 300.00 g of 10 wt % Na$_2$CO$_3$ was then added, resulting in separation. To the organic phase, 600.00 g of 5 wt % NaHCO$_3$ was added, resulting in separation. To the organic phase, 300.00 g of water was added, resulting in separation. This separation operation was repeated twice. From the organic phase, a solvent was distilled off under reduced pressure, and the residue was then dried at 40° C. under reduced pressure. 30.77 g of diethyl monoglycidyl isocyanurate of Formula (1-1) above was obtained as a white solid (yield: 95.8%). This compound was subjected to $^1$H NMR measurement (500 MHz, CDCl$_3$). δ 4.16 (dd, 1H), 3.99 (dd, 1H), 3.96 (q, 4H), 3.26 (dddd, 1H), 2.82 (dd, 1H), 2.70 (dd, 1H), 1.25 (t, 6H)

Example 2

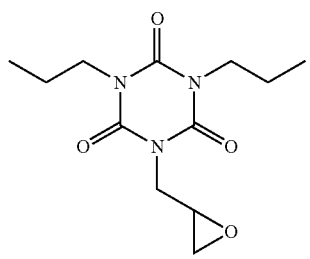

(1-2)

36.00 g of dipropyl monoallyl isocyanurate obtained in Synthesis Example 2 and 270.00 g of chloroform were mixed and stirred at 25° C. To the mixture, 45.28 g of m-chloroperbenzoic acid (available from Tokyo Chemical Industry Co., Ltd.) was added. The mixture was stirred at 25° C. for 134 hours to obtain a reaction solution. To the reaction solution, 360.00 g of chloroform was added. With stirring, 720.00 g of 5 wt % NaHCO$_3$ was added dropwise, and separation was carried out. To the resulting organic phase, 360.00 g of 10 wt % Na$_2$SO$_3$ was added, resulting in separation. To the organic phase, 720.00 g of 5 wt % NaHCO$_3$ was added, resulting in separation. To the organic phase, 360.00 g of water was added, resulting in separation. This separation operation was repeated twice. From the organic phase, a solvent was distilled off under reduced pressure, and the residue was then dried at 40° C. under reduced pressure. 37.93 g of dipropyl monoglycidyl isocyanurate of Formula (1-2) above was obtained as a white solid (yield: 98.0%). This compound was subjected to $^1$H NMR measurement (500 MHz, CDCl$_3$). δ 4.17 (1H, dd), 4.00 (1H, dd), 3.86 (4H, t), 3.25 (1H, dddd), 2.81 (1H, dd), 2.69 (1H, dd), 1.68 (4H, tq), 0.95 (6H, t)

Example 3

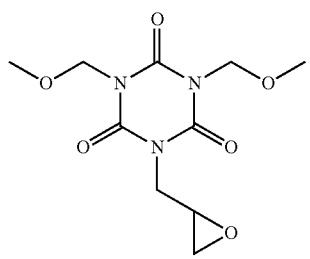

(2-1)

30.00 g of dimethoxymethyl monoallyl isocyanurate obtained in Synthesis Example 3 and 225.00 g of chloroform were mixed and stirred at 25° C. To the mixture, 37.16 g of m-chloroperbenzoic acid (available from Tokyo Chemical Industry Co., Ltd.) was added. The mixture was stirred at 25° C. for 172 hours to obtain a reaction solution. To the reaction solution, 300.00 g of chloroform was added. With stirring, 600.00 g of 5 wt % NaHCO$_3$ was added dropwise, and separation was carried out. To the resulting organic phase, 300.00 g of 10 wt % Na$_2$SO$_3$ was added, resulting in separation. To the organic phase, 600.00 g of 5 wt % NaHCO$_3$ was added, resulting in separation. To the organic phase, 300.00 g of water was added, resulting in separation. This separation operation was repeated twice. From the organic phase, a solvent was distilled off under reduced pressure, and the residue was then dried at 40° C. under reduced pressure. 29.23 g of dimethoxymethyl monoglycidyl isocyanurate of Formula (2-1) above was obtained as a white solid (yield: 91.7%). This compound was subjected to $^1$H NMR measurement (500 MHz, CDCl$_3$). δ 5.35 (s, 4H), 4.35 (dd, 1H), 4.19 (dd, 1H), 4.67 (s, 6H), 3.28 (dddd, 1H), 2.82 (dd, 1H), 2.71 (dd, 1H)

Example 4

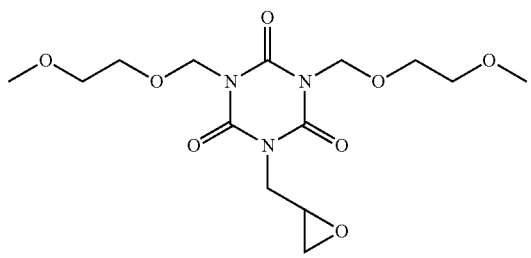

(3-1)

20.00 g of dimethoxyethoxymethyl monoallyl isocyanurate obtained in Synthesis Example 4 and 150.00 g of chloroform were mixed and stirred at 25° C. To the mixture, 18.45 g of m-chloroperbenzoic acid (available from Tokyo Chemical Industry Co., Ltd.) was added. The mixture was stirred at 25° C. for 152 hours to obtain a reaction solution. To the reaction solution, 200.00 g of chloroform was added. With stirring, 400.00 g of 5 wt % NaHCO$_3$ was added dropwise, and separation was carried out. To the resulting organic phase, 200.00 g of 10 wt % Na$_2$SO$_3$ was then added, resulting in separation. To the organic phase, 400.00 g of 5 wt % NaHCO$_3$ was added, resulting in separation. To the organic phase, 200.00 g of water was added, resulting in separation. This separation operation was repeated twice. From the organic phase, a solvent was distilled off under reduced pressure, and the residue was then dried at 40° C. under reduced pressure. 18.34 g of dimethoxyethoxymethyl monoglycidyl isocyanurate of Formula (3-1) above was obtained as a liquid (yield: 87.6%). This compound was subjected to $^1$H NMR measurement (500 MHz, CDCl$_3$). δ 5.42 (s, 4H), 4.18 (dd, 1H), 4.00 (dd, 1H), 3.82 (t, 4H), 3.52 (t, 4H), 3.34 (s, 6H), 3.25 (dddd, 1H), 2.82 (dd, 1H), 2.71 (dd, 1H)

Example 5

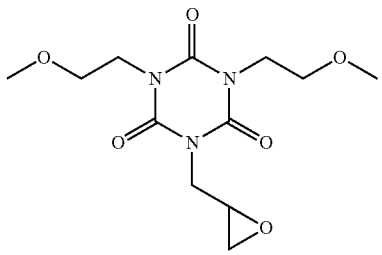

(2-2)

31.00 g of dimethoxyethyl monoallyl isocyanurate obtained in Synthesis Example 5 and 232.50 g of chloroform were mixed and stirred at 25° C. To the mixture, 34.62 g of m-chloroperbenzoic acid (available from Tokyo Chemical Industry Co., Ltd.) was added. The mixture was stirred at 25° C. for 152 hours to obtain a reaction solution. To the reaction solution, 310.00 g of chloroform was added. With stirring, 620.00 g of 5 wt % $NaHCO_3$ was added dropwise, and separation was carried out. To the resulting organic phase, 310.00 g of 10 wt % $Na_2SO_3$ was then added, resulting in separation. To the organic phase, 620.00 g of 5 wt % $NaHCO_3$ was added, resulting in separation. To the organic phase, 310.00 g of water was added, resulting in separation. This separation operation was repeated twice. From the organic phase, a solvent was distilled off under reduced pressure, and the residue was then dried at 40° C. under reduced pressure. 30.44 g of dimethoxyethyl monoglycidyl isocyanurate of Formula (2-2) above was obtained as a liquid (yield: 93.0%). This compound was subjected to $^1$H NMR measurement (500 MHz, $CDCl_3$). δ 4.19-4.12 (5H, m), 4.01 (1H, dd), 3.62 (4H, t), 3.35 (6H, s), 3.25 (1H, dddd), 2.81 (1H, dd), 2.69 (1H, dd)

Comparative Example 1

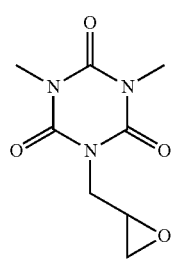

(10)

30.00 g of dimethyl monoallyl isocyanurate obtained in Synthesis Example 6 and 300.00 g of dichloromethane were mixed and stirred at 25° C. To the mixture, 56.51 g of m-chloroperbenzoic acid (available from Tokyo Chemical Industry Co., Ltd.) was added. The mixture was stirred at 25° C. for 64.5 hours to obtain a reaction solution. To the reaction solution, 300.00 g of chloroform was added. With stirring, 600.00 g of 5 wt % $NaHCO_3$ was added dropwise, and separation was carried out. To the organic phase, 600.00 g of 10 wt % $Na_2SO_3$ was added, resulting in separation. To the organic phase, 600.00 g of 5 wt % $NaHCO_3$ was added, resulting in separation. To the organic phase, 600.00 g of water was added, resulting in separation. This separation operation was repeated twice. From the organic phase, a solvent was distilled off under reduced pressure, and the residue was then dried at 40° C. under reduced pressure. 27.64 g of dimethyl monoglycidyl isocyanurate of Formula (10) above was obtained as a white solid (yield: 73.1%).

[Evaluation of Solubility in Solvent]

To 0.1 g of the compound obtained in each of Examples 1 to 5 and Comparative Example 1, 0.4 g of propylene glycol monomethyl ether was added to obtain a 20 wt % solution. The solution was stirred at 25° C. for 10 minutes. The solubility of the solution was visually confirmed. As shown in Table 1, the solubility of all the compounds synthesized in Examples 1 to 5 was improved as compared with the compound obtained in Comparative Example 1. In Table 1, x represents a clouded solution, and ○ represents a clear solution in which a precipitate is not produced.

TABLE 1

|  | Comparative Example 1 | Example 1 | Example 2 | Example 3 | Example 4 | Example 5 |
| --- | --- | --- | --- | --- | --- | --- |
| Solubility | X | ○ | ○ | ○ | ○ | ○ |

INDUSTRIAL APPLICABILITY

For example, the monoglycidyl isocyanurate compound of the present invention can be applied to an anti-reflective coating-forming composition for lithography, a resist underlayer film-forming composition, a resist upper layer film-forming composition, a photocurable resin composition, a thermosetting resin composition, a flattened film-forming composition, an adhesives composition, and other compositions. The monoglycidyl isocyanurate compound of the present invention can be used as a raw material compound in synthesis of an oligomer or polymer used for the composition.

The invention claimed is:

1. A monoglycidyl isocyanurate compound of Formula (3) below:

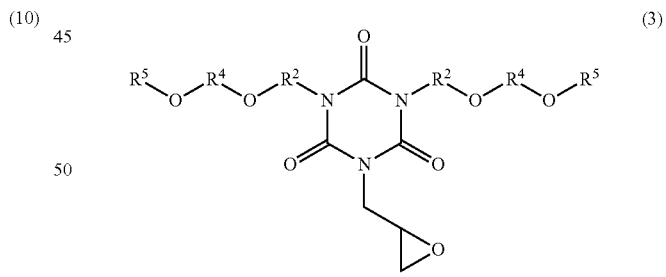

(3)

wherein two $R^2$s are each a $C_{1-5}$ alkylene group, two $R^4$s are each a $C_{1-2}$ alkylene group, and two $R^5$s are each a $C_{1-2}$ alkyl group.

2. The monoglycidyl isocyanurate compound according to claim 1, wherein the two $R^2$s are each a $C_{1-2}$ alkylene group.

3. The monoglycidyl isocyanurate compound according to claim 1, wherein the monoglycidyl isocyanurate compound of Formula (3) is liquid at normal temperature under normal pressure when the total number of carbon atoms and oxygen atoms of a —$R^2OR^4OR^5$ group in Formula (3) is four or more.

4. A method for producing the monoglycidyl isocyanurate compound according to claim 1 comprising the steps of obtaining a reaction intermediate of the following Formula (3'):

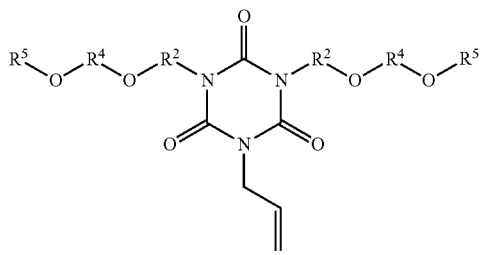

wherein two $R^2$s, two $R^4$s, and two $R^5$s each have the same definition as that in claim 1 from monoallyl isocyanuric acid, and reacting the reaction intermediate of Formula (3') with an oxidant.

5. The method for producing the monoglycidyl isocyanurate compound according to claim 4, wherein the reaction intermediate of Formula (3') is obtained by reacting the monoallyl isocyanuric acid with a compound of the following Formula (c):

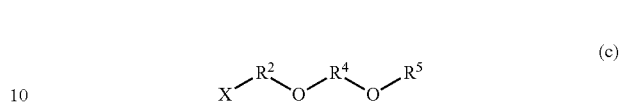

wherein X is a chloro group, a bromo group, or an iodo group, and $R^2$ is a $C_{1-5}$ alkylene group, $R^4$ is a $C_{1-2}$ alkylene group, and $R^5$ is a $C_{1-2}$ alkyl group.

6. The method for producing the monoglycidyl isocyanurate compound according to claim 4, wherein the oxidant is m-chloroperbenzoic acid or hydrogen peroxide.

* * * * *